US00PP18625P3

(12) United States Plant Patent
Pinhas et al.

(10) Patent No.: US PP18,625 P3
(45) Date of Patent: Mar. 18, 2008

(54) GRAPE PLANT NAMED 'ARRAFOURTEEN'

(50) Latin Name: ***Vitis* sp.**
Varietal Denomination: Arrafourteen

(75) Inventors: Spiegel-Roy Pinhas, Ramat Gan (IL); Baron Izhak, Rehovot (IL); Sahar Hachman, Rehovot (IL); Perl Avihai, Rishon LeZion (IL)

(73) Assignee: The Agricultural Research Organization, Bet-Dagan (IL)

( * ) Notice: Subject to any disclaimer, the term of this patent is extended or adjusted under 35 U.S.C. 154(b) by 94 days.

(21) Appl. No.: 11/413,410

(22) Filed: Apr. 28, 2006

(65) Prior Publication Data

US 2007/0016988 P1 Jan. 18, 2007

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H Para
(74) *Attorney, Agent, or Firm*—Christie, Parker & Hale, LLP

(57) ABSTRACT

A new and distinct variety of Grapevine, designated 'Arrafourteen', characterized by strong vegetation, on own root and when grafted, red berry color with very uniform coverage and color, somewhat smaller bunches, and very juicy berries with pleasant taste and aroma.

2 Drawing Sheets

CROSS-REFERENCE TO RELATED APPLICATIONS

This application claims priority to South African PBR Registration Application No. VL 2005/6339, filed Apr. 29, 2005, the disclosure of which is incorporated herein by reference.

Botanical classification/cultivar denomination: *Vitis* sp. cultivar Arrafourteen.

BACKGROUND OF THE INVENTION

The present invention relates to a new and distinct variety of Grapevine, botanically known as *Vitis* sp., and hereinafter referred to by the name 'Arrafourteen'.

SUMMARY OF THE INVENTION

'Arrafourteen' was discovered as a red fruit mutation amount the parent 'Prime 125' seedless cultivar.

It has been asexually reproduced at Nancy Farms in Paarl, South Africa, by budwood vegetative propagation. Observations made on 'Arrafourteen' since 2001 have shown that the unique features of this new Grapevine are stable and reproduced true to type in successive generations.

The new variety differs from other cultivars known to the inventor, including its parents, in the following traits, which have been repeatedly observed and are determined to be the unique and stable characteristics of 'Arrafourteen':

1. Strong vegetation variety, on own root and when grafted;
2. Produces small bunches compared to parent Prime Seedless;
3. Berry color is red, in comparison with the green of the Prime Seedless;

4. Ripening time is 2–3 days later compared to the green Prime Seedless;
5. Midseason variety, ripening in the last half of June.

These characteristics in combination distinguish 'Arrafourteen' as a new and distinct Grapevine cultivar. All observations were made from four year old specimens grown in Paarl, South Africa, from 2001 till 2005.

BRIEF DESCRIPTION OF ILLUSTRATIONS

The accompanying photographic illustrations show typical specimens of four year old specimens of the new variety, in color as nearly true as it is reasonably possible to make in a color illustration of this character. Colors in the photograph may differ from the color values cited in the detailed botanical description below, which accurately describes the colors of the new Grapevine.

Figure 1:
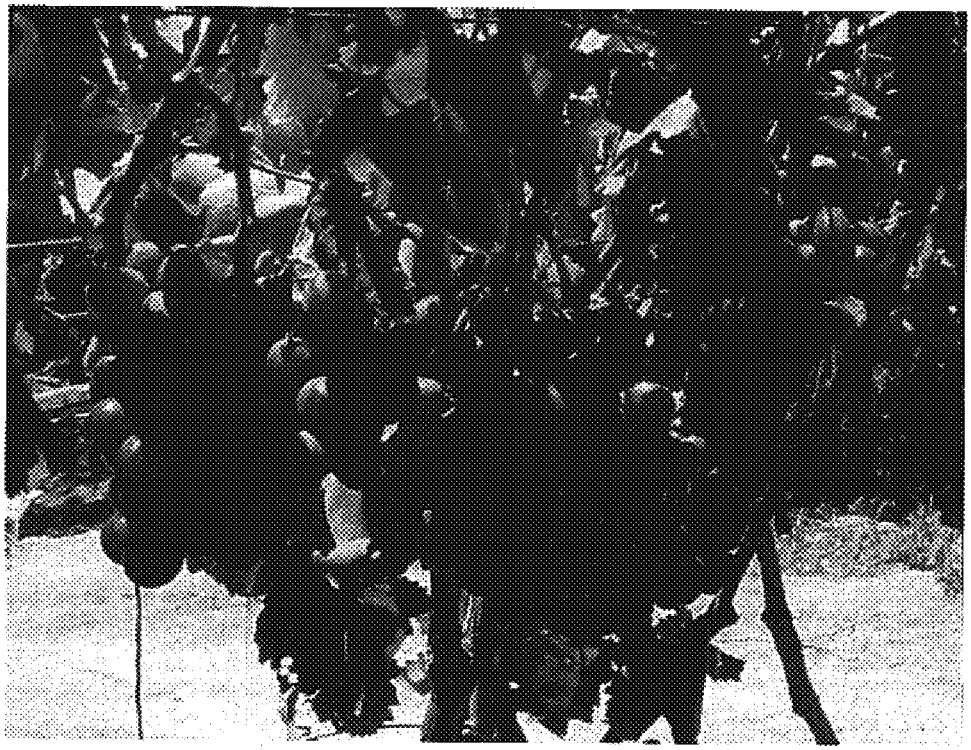

FIG. 1 comprises leaves, stems and grapes of 'Arrafourteen'.

Figure 2:
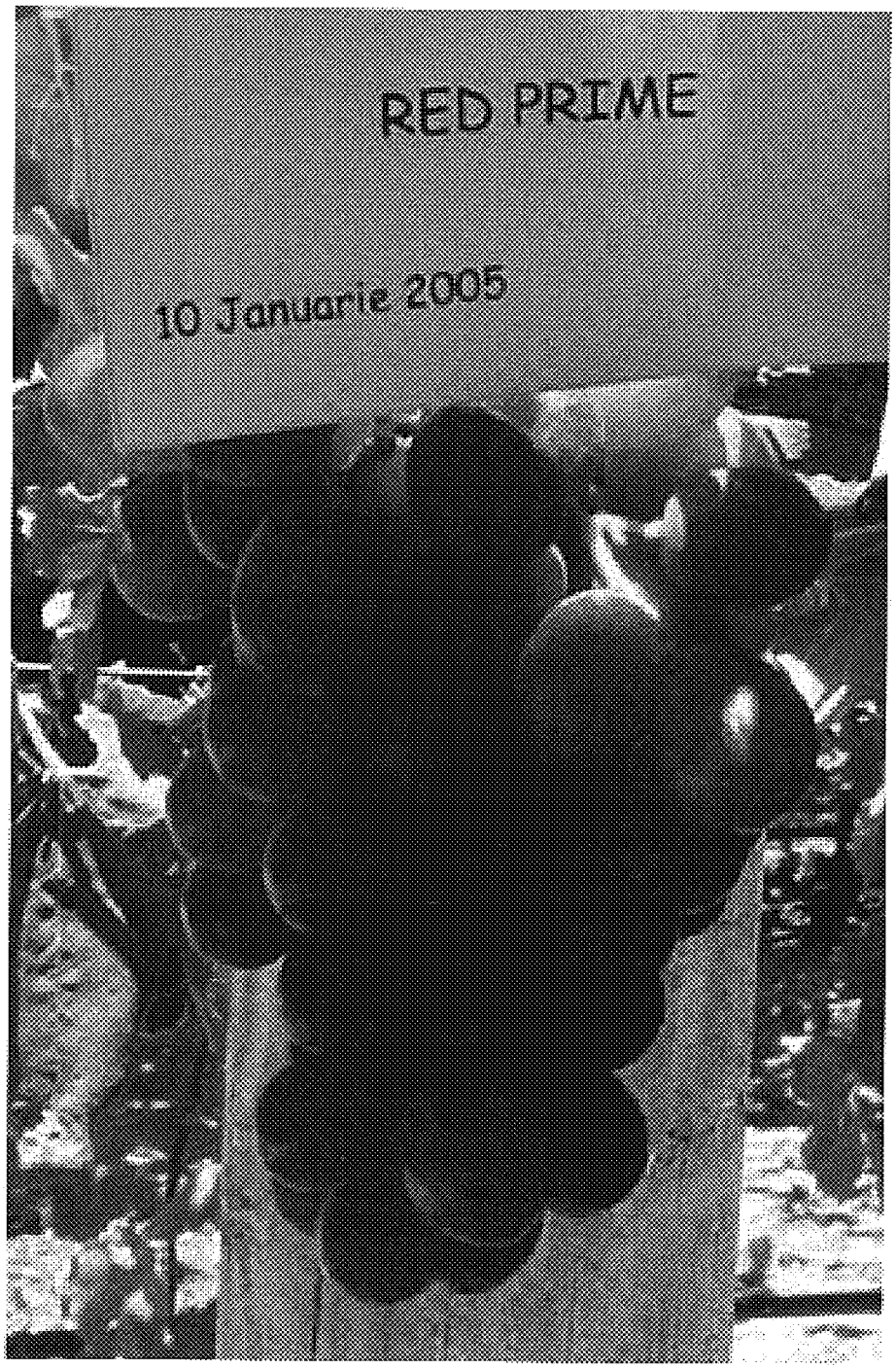

FIG. 2 comprises a close-up of a bunch of 'Arrafourteen'.

DESCRIPTION OF THE NEW VARIETY

Referring now specifically to the new and distinct variety of Grapevine, the following is a detailed description of 'Arrafourteen' with color description where indicated by reference to The Royal Horticultural Society Colour Chart, except where common terms of color definition are employed.

The new variety of Grapevine as herein described may vary in slight detail due to climatic, soil and cultural conditions under which the variety may be grown, the present description being of four year old specimens of the variety as grown from its own root at Paarl, South Africa, between 2001 and January of 2005.

Plant characteristic:

*Form.*—Upright with canopy of four feet on either side of the trunk, vines of 157 cm to 197 cm in width perpendicular to a row.

*Growth.*—Low vigor, particularly weak during flowering.

Vegetative characteristics:

*Trunk.*—Size — medium developed for age, ranges from 46 mm to 88 mm. Surface texture — rough. Color — Greyed Green near group 197.

*Canes.*—Form of growing tip — half opened. Cross-sectional form — circular to slightly eliptical. Thickness — small to medium from 8 mm to 17 mm diameter average. Surface texture — relatively smooth with occasional ribbing. Length — slightly less than average with an average joint frequency of 60 mm to 160 mm. Shoot color — Yellow Green Group near 153A, intermixed with bands of Orange-Red near group 34. Form of tendrils — predominantly trifid, with occasional bifid. Distribution of tendrils — discontinuous. Length of tendrils — average length 11.5 cm to 18 cm.

*Shoot.*—Young Shoot: Form of tip: half open. Anthocyanin coloration of tip: medium. Density of prostrate hairs on tip: very sparse. Density of erect hairs on tip: very sparse. Color: green 146-D strips greyed orange 175-B. Shoot: Attitude (habit): semi-erect. Color of dorsal side of internode (well illuminated); green 146-D strips greyed orange 175-B. Color of ventral side of node internode (without direct sunlight): green 146-D strips greyed orange 175-B. Color of dorsal side of node (well-illuminated): green 146-D strips greyed orange 175-B. Color of ventral side of node (without direct sunlight): green 146-D strips greyed orange 175-B. Density of erect hairs on node: sparse. Erect hairs on internode: present. Density of prostrate hairs on internode: absent. Number of consecutive tendrils: three or more. Length of tendril: long. Woody Shoot: Surface: edged. Main color: yellowish brown 2/orange 165-B strips of orange 166C.

*Leaf general.*—Form — generally pentagonal. Shape of blade — kidney shape with five lobes. Marginal form — broadly serrate. Length of leaf — average mature leaf ranges from 115 to 152 mm as measured from petiolar junction to apex of central lobe. Width of leaf — average width 56 mm to 94 mm. Surface texture — relatively smooth. Top color — Green Group near 143A. Bottom color — Yellow-Green Group near 145A. Stick color — Yellow-Green Group near 152A. Anthocyanin coloration on main veins on upper side of blade (Recorded on leaves above the cluster at the medium third of shoot) — Yellow-Green Group near 144C. Profile (cross-section at the middle of the leaf blade) — flat. Lobe apices form — acute. Shape of teeth (Recorded on the lateral lobe) — Both sides convex. Length of teeth: largest range from 2 to 4 mm. Ratio length/width of teeth — Medium. Thickness vein — average. General shape of petiole sinus (Degree of the opening of the petiole sinus) — distinctly "V" shaped with lobes overlapping with no particularities of petiole sinus. Tooth of petiole sinus — both sides convex and medium in length. Length of petiole to middle vein — equal. Length petiole — average length 78 mm to 109 mm. Thickness petiole — varies from 2 to 3 mm. Stipules — absent. Young Leaf: Color of upper surface (recorded on the first 4 distal unfolded leaves): yellow green 144B. Density of prostrate hairs between veins (recorded on the lower surface of the 4th distal unfolded leaf): very sparse. Density of erect hairs between veins (recorded on the lower surface of the 4th distal unfolded leaf): very sparse. Density of prostrate hairs on main veins (recorded on the lower surface of the 4th distal unfolded leaf): very sparse. Density of erect hairs on main veins (recorded on the lower surface of the 4th distal unfolded leaf): very sparse. Mature Leaf: Size of blaze (recorded on mature leaves above the cluster within the medium third of shoot): medium. Shape of blade: wedge shaped. Number of lobe: three. Anthocyanin coloration on main veins on upper side of blade (recorded on leaves above cluster at the medium third of shoot): medium green 144A. Profile (cross-section at the middle of the leaf blade): V-shaped. Blistering of blade upper surface: absent. Shape of teeth (recorded on lateral lobe): both sides straight. Length of teeth: short. Ratio length/width of teeth: small. General shape of petiole sinus (degree of the opening of the petiole sinus): half open. Tooth of petiole sinus: absent. Petiole sinus limited by veins: absent. Shape of upper lateral sinus (degree of the opening of the upper lateral sinus). A sinus is defined as a clear interruption of teeth on the leaf margin. The upper lateral sinus is located between the middle vein and next lateral main vein: closed. Depth of upper lateral sinus: shallow. Density of prostrate hairs between veins (recorded on the lower side of blade): sparse. Density of erect hairs between veins (recorded on the lower side of blade): sparse. Density of prostate hairs on main veins (recorded on the lower side of blade): sparse. Density of erect hairs on main veins (recorded on the lower side of blade): sparse. Density of prostate hairs on main veins (recorded on the upper surface of the blade): present. Length of petiole compared to middle vein: slightly longer.

Inflorescence and fruit:

*Inflorescence.*—Sex of flower hermaphroditic medium length.

*Flower.*—Form — cluster of small to medium size. Location — first floral cluster occurs from third to sixth joint. Length — bloom ranges from 30 mm to 35 mm from base of peduncle to tendril and from 18 to 30 mm from tendril to first rachis branch. Floral cluster length — ranges from 11 to 18.5 cm without peduncle. Floral cluster width — ranges from 6 to 12 cm. Stamens form — upright. Anthers size — average. Pollen quantity — abundant. Calyptra — separates completely from base of flower.

*Bunch.*—Size (without peduncle) — medium, length ranges from 14 to 22.8 cm, width ranges from 10 to 15 cm. Density — medium. Length of peduncle — medium, average length 18 to 44 mm, thickness 2.5 to 4.5 mm. Shape — conical. Number of berries — approximately 70 to 110 berries per bunch. Color of peduncle — Yellow-Green Group near 144C.

*Berry.*—Size — medium diameter ranges from 18 to 24 mm, length ranges from 19 to 24 mm. Shape — obtuse. Presence of seed — absent. Skin color — light-dependent, recorded on berries which are exposed directly to sun, greyed red 179 A. Anthocyanin coloration of flesh: slightly colored. Skin texture — medium thick skin. Weight — 10 berries, about 47 g. Firmness of flesh (Weight necessary for cracking the berries) — medium. Juiciness of flesh — very slightly juicy. Aroma — special, pleasant. Particular flavor — none. Pedicel size — length ranges from 4 to 11 mm, thickness ranges from 1.5 to 2.8 mm at mid pedicel. Ease of detachment from pedicel — difficult. Seed length: short. Transversal ridges on sides: absent.

*Plant descriptors.*—All information below based on growing the variety in the South Africa.

*Time of bud burst* (only varieties for fruit production).—Early. In the first week of November.

*Inflorescence.*—Cluster of small to medium size, 1.1 to 2.

*Time of berry ripening* (*veraison*).—Medium, early January.

*Bunch length* (*without peduncle*).—Intermediate, length ranges from 14 to 22.8 cm.

*Berry thickness of skin* (*thickness of epidermis plus hypodermis*).—Medium thick.

*Pedicle length.*—Intermediate.

*Visibility of hilum.*—Unclear.

*Physiological stage of full maturity of the berry* (*maximum sugar content of the berry*).—Late.

*Growth of auxiliary shoots.*—Strong.

*Shoot.*—Length of internodes: medium.

*Percentage of berry set.*—Medium.

*Single bunch weight.*—High.

*Single berry weight.*—High.

*Bunch weight.*—High.

*Sugar content of must* (%).—High.

*Total acid content of must.*—Very low.

*Market use information.*—Fresh table grape, high quality seedless for fresh consumption, shipping quality of the fruit is very good both in storage and transportation stem retains turgidity for extended period.

*Resistance/susceptibility to disease and pest.*—No difference from other *Vitis Venifera* varieties.

Comparison to flame seedless: Prime seedless is a popular green grape in the USA. It is early, crunchy and pleasant to eat.

*Prime seedless is different from the new variety by the following.*—'Arrafourteen' ripening time is two to three days later than Prime seedless; 'Arrafourteen' has a smaller bunch size than green Prime seedless; and 'Arrafourteen' has a uniform red color fully covered from early stages of ripening, while Prime seedless are green.

We claim:

1. A new and distinct variety of grapevine, botanically known as *Vitis* sp., identified as 'Arrafourteen', substantially as shown and described herein.

* * * * *